United States Patent [19]

Urist

[11] Patent Number: 4,563,489

[45] Date of Patent: Jan. 7, 1986

[54] BIODEGRADABLE ORGANIC POLYMER DELIVERY SYSTEM FOR BONE MORPHOGENETIC PROTEIN

[75] Inventor: Marshall R. Urist, Pacific Palisades, Calif.

[73] Assignee: University of California, Berkeley, Calif.

[21] Appl. No.: 579,034

[22] Filed: Feb. 10, 1984

[51] Int. Cl.[4] .................... A61K 37/02; A61K 35/32; C07G 7/00
[52] U.S. Cl. ........................................ 524/21; 524/17; 523/115; 514/21; 424/78; 604/891; 623/16
[58] Field of Search .................... 524/17, 21; 523/113, 523/115, 116, 117; 424/177, 359, 78; 604/890, 891; 3/1.9

[56] References Cited

U.S. PATENT DOCUMENTS

| | | | |
|---|---|---|---|
| 4,394,370 | 7/1983 | Jefferies | 424/15 |
| 4,428,082 | 1/1984 | Naficy | 3/36 |
| 4,430,760 | 2/1984 | Smestad | 128/926 |

Primary Examiner—John Kight
Assistant Examiner—Nathan M. Nutter

[57] ABSTRACT

Disclosed is a biodegradable polylactic acid polymer delivery system for delivery of bone morphogenic protein (BMP) to induce formation of new bone in viable tissue. The delivery composition is substantially pure BMP in combination with a biodegradable polylactic acid polymer and it is prepared by admixing the BMP with the biodegradable polymer. The composition is implanted in viable tissue where the BMP is slowly released and induces formation of new bone.

13 Claims, 6 Drawing Figures

Roentgenograms Of Mouse Thighs Showing
Induced Bone Formation In Response To
5mg. Of bBMP/20mg.(Right); No Bone
Formation Is Induced By 20mg Of PL Alone (Left).

ROENTGENOGRAMS OF MOUSE THIGHS SHOWING INDUCED BONE FORMATION IN RESPONSE TO 5mg. OF bBMP/20mg. (RIGHT); NO BONE FORMATION IS INDUCED BY 20mg OF PL ALONE (LEFT).

PHOTOMICROGRAPH OF DEPOSITS OF NEW BONE FORMED IN RESPONSE TO bBMP-PL, 21 DAYS AFTER IMPLANTATION IN MOUSE THIGH MUSCLE. NOTE: bBMP-PL (P); BONE (B); BONE MARROW (R).

ROENTGENOGRAMS OF MOUSE THIGH SHOWING IMPLANTS OF 5mg. OF bBMP (LEFT) AND 5 mg. OF BMP/20mg. OF bBMP-PL (RIGHT). NOTE THE RELATIVELY HIGH RADIODENSITY AND YIELD OF NEW BONE FROM THE bBMP-PL.

PHOTOMICROGRAPHY OF CHONDROOSTEOID (C) SURROUNDED BY NEW BONE (ARROW) AND BONE MARROW, 21 DAYS AFTER IMPLANTATION OF BMP-PL.

Photomicrography, High Magnification of Unabsorbed Remnants of BMP-PL(P). Note: (Arrow) New Bone Surrounded By Bone Marrow Photomicrograph Showing Osteoid Tissue (O) Deposited on Surfaces of BMP (PL). Note: Bone and Bone Marrow Surrounding Remnants of BMP-PL (Arrows).

BIODEGRADABLE ORGANIC POLYMER DELIVERY SYSTEM FOR BONE MORPHOGENETIC PROTEIN

BACKGROUND OF THE INVENTION

This invention was made with Government support under Grant No. DE 02103 awarded by the Department of Health and Human Services. The Government has certain rights in this invention.

This invention relates to compositions and methods for delivering bone morphogenetic protein (BMP) to viable bone and other skeletal tissues. More specifically, the invention relates to such delivery systems for BMP utilized in bone implants, and comprises compositions that are admixtures of physiologically acceptable biodegradable organic polymers and BMP. The delivery composition may thus be applied to defective bone tissue and other viable tissue to induce formation of new bone. The invention also relates to the preparation of such bone implant compositions and the method of using such compositions as bone implants.

BMP is a relatively low molecular weight protein or protein implant that is isolated from dentin, bone and other skeletal tissues by chemical extraction and differentiation percipitation. BMP induces perivascular mesenchymal type cells to differentiate into cartilage and bone by endochrondal ossification. The target of BMP is connective tissue cells (pericytes) surrounding small blood vessels of bone marrow and muscle attachments to bone. BMP may be isolated in relatively pure form by processes described in U.S. Pat. No. 4,294,753 and in copending patent application Ser. No. 260,726 filed May 5, 1981 now U.S. Pat. No. 4,455,256. BMP, and processes for its isolation and more complete purification are further described in Ser. No. 523,606 filed Aug. 16, 1983. The disclosures in said patent and applications are incorporated herein by reference.

It is disclosed in the aforementioned patent and patent applications that BMP may be implanted directly into a bone defect where it stimulates differentiation of connective tissue into bone and thereby repairs the defect. After about six months remodeling is substantially complete, and about 1 gram of bone is produced for each milligram of BMP implanted. Such levels of bone induction have been observed when a relatively high proportion of BMP is initially used in the implant. Otherwise, at lower total BMP levels new bone induction is substantially reduced or no induction at all takes place. For example, when up to 1 mg. of BMP was inserted into a mouse muscle pouch, BMP was rapidly absorbed and did not induce formation of grossly visible deposits of new bone. Moreover, the nature (metabolic rate) of the animal subject under treatment is a major determinant as to the minimum quantity of BMP that will induce new bone formation.

It is therefore, an object of the present invention to develop a delivery system for BMP which increases the yield of bone generation per unit weight of BMP. A further object is the development of a physiologically acceptable biodegradable system which is metabolized so that the regenerated bone eventually will be substantially free of foreign material.

SUMMARY OF THE INVENTION

The present invention provides a composition and method for greatly increasing the amount of new bone induced to be formed by a given amount of substantially pure BMP, and producing new bone which will eventually be substantially free of foreign material. Particularly, the threshold quantity of BMP required to induce new bone formation is substantially reduced and the delivery system for BMP is metabolized to remove it from the bone. It has now been discovered that a delivery system for BMP comprising a physiologically acceptable, biodegradable polylactic acid and BMP allows the BMP to be delivered on a sustained basis to the host tissue, preferably bone tissue with the expectation that bone formation will be induced for a substantial period. Yet, the delivery system is biodegradable within the viable animal protein and thus eventually removed and eliminated. In addition, other physiologically acceptable, biodegradable organic polymers which are structurally equivalent to polylactic acid can be used as the delivery system for BMP. For example, such physiologically acceptable biodegradable, structurally equivalent organic polymers include but are not limited to poly(hydroxy organic carboxylic acids) eg. poly(hydroxy aliphatic carboxylic acids), polyglycollic acid, polyglactin, polyglactic acid and poly aldonic acids. The especially preferred polymer is polylactic acid (PL).

The BMP composition of this invention provides sustained delivery of BMP and causes stimulation of host bed new bone formation for a period believed to be on the order of months. Moreover, the quantity of bone that is induced for a given amount of BMP implanted in the BMP-PL polymer delivery composition described herein has been found to be significantly higher when compared with new bone formation induced by BMP in the absence of the polymer. For example, as shown herein, 0.1 mg. of BMP in combination with 0.1 mg. of powder polylactic acid (PL) induced grossly visible deposits of new bone in a mouse muscle pouch, as detected by roentgenogram examination whereas implants of 0.1 mg. quantities of BMP without PL did not produce any new bone. Thus, the present invention allows for substantially reduced quantities of BMP to be used in bone implants, and yet results in the induced formation of significant quantities of new bone. Histological sections at 2 to 4 day intervals from 2 to 21 days after the operation showed progressive dissolution and absorption of the implants. The observation that the BMP-PL polymer composition of this invention induces formation of large quantities of new bone from smaller quantities of BMP compared to implants of BMP dispersed in the tissues without PL polymer suggests that slow absorption in a locally sustained concentration gradient of BMP enhances the bone morphogenetic response.

BRIEF DESCRIPTION OF THE DRAWINGS

The figures illustrate the physiological results produced by the composition of the invention.

DETAILED DESCRIPTION OF THE INVENTION

Figure 1:
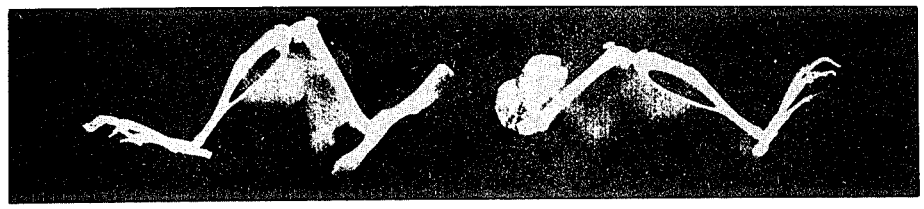
FIG. 1 shows. Roentgenograms of mouse thighs showing induced bone formation in response to 5 mg of bBMP/20 mg PL (right); no bone formation is induced by 20 mg of PL alone.
Figure 4:
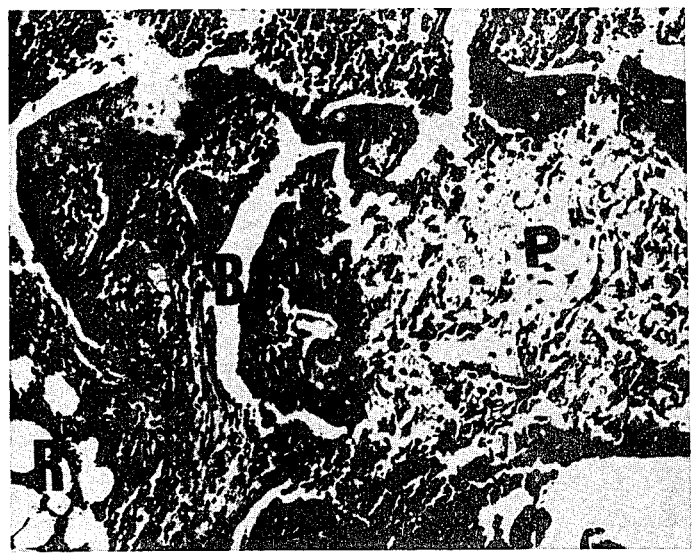
FIG. 4 shows a photomicrograph of deposits of new bone formed in response to bBMP-PL, 21 days after implantation in mouse thigh mouscle. Note: bBMP-PL (P); bone (B); bone marrow (R).

BMP delivered by the system of this invention induces formation of bone by the host bed connective tissues surrounding the implant into bone. Other advantages of the BMP-PL polymer sustained delivery system include, (1) along term proliferation of new bone for substantial reinforcement of the host bone bed, (2) ingrowth of bone into the implant etc. surfaces and interior crevices containing the composition, (3) prevention of loosening of joint implants in young active patients and (4) metabolism and removal of the organic polymer system after its function has been performed.

The biodegradable organic polymer, PL, is a non-immunogenic polymer that may be produced by methods described in U.S. Pat. No. 2,703,316, (1959) and other foreign patents, and is approved by the U.S. food and Drug Agency for implantation in the body in the forms of suture material. The BMP-PL composite is designed for a biodegradable delivery system. In nature, bone collagen and other bone high MW proteins represent that delivery system for endogenous BMP. For exogenous BMP for treatment of patients with endogenous BMP deficiencies it is advantageous to use a non-immunogenic, non proteinacious delivery system. Because these high MW proteins are immunogenic, while the biodegradable polymer PL is non-immunogenic, the BMP-biodegradable PL polymer composite of the invention is a highly efficient delivery system. Furthermore BMP implanted free without a delivery system in tissues is so rapidly absorbed that mg doses are necessary to induce bone formation. In contrast BMP with the delivery system, in the form of the BMP-biodegradable PL composite, is effective in ug doses.

Briefly, the method for preparing the implant material of the present invention comprises dissolving the physiologically acceptable biodegradable PL polymer in a solvent such as ethanol, acetone or chloroform, admixing the polymer solution with BMP to form a dispersion of BMP in the polymer solution and precipitating the composite by adding a second solvent which causes precipitation of the polymer, or lyophylizing the dispersion or otherwise treating the dispersion to remove it from solvent and form the composite. After composite formation, it is filtered, pressed or otherwise processed to remove the solvent, and the resulting composite solid is formed into the desired shape for implantation. Generally, this method forms the active delivery composition of the invention. Other additives may be included in the admixture, each for its own particular function. For example, there may also be included in the composition, radioopacifying agents, antibiotics, prosthesis devices, and the like. In preferred embodiments, the BMP-biodegradable polymer delivery composition is formed into a dough, rod, film, flake or otherwise shaped as desired.

BMP is prepared in powder form as set forth in the above referenced patent and patent applications. Either purified BMP or its co-precipitate with tricalcium phosphate may be used. Shortly before use, the BMP and biodegradable PL polymer powders are mixed together with solvent as described above. While still dispersed/dissolved in solvent, the composition may be formed into small pellets, flakes, platelets etc. by casting in molds and allowed to dry or harden. The composition may be supplemented with other agents as desired, such as radioopacifying agents (barium sulfate) and antibiotics (e.g., gentamyicin or silver sulfate). Such additives have been known and used in connection with bone cement materials. See, for example, J. Bone Joint Surg., 63A;798, 1981, "The Depot Administration of Penicillin G and Gentamyicin in Acrylic Bone Cement," Hoff et al.,; and, Clin. Orthop., 169: 264–268, 1982, "Silver Antibacterial Cement Comparison with gentamycin in experimental osteomyeolitis," Dueland et al. The proportions of the additive to be used are well known, for example between 6 and 12 percent by weight of the composition may be barium sulfate.

Biodegradable organic polymers such as PL or chemical derivatives and analogs of PL are commonly used in manufacture of absorbable suture material but they have not been used heretofor for a delivery system for BMP because BMP has been isolated only recently. Accordingly such derivatives and analogs are functional equivalents of PL in the composition of the invention. The BMP-biodegradable PL polymer delivery system has applications in enhancing bone repair in all kinds of orthopedic reconstructive operations.

The literature on biodegradable drug delivery systems has been reviewed in detail by Pitt et al (1980). Pitt, Colin G., Marks, Thomas A., Schindler, Anton. "Biodegradable Drug Delivery Systems Based on Aliphatic Polyesters: Application To Contraceptives and Narcotic Antagonists." Published by Academia Press, Inc. 1980 for the National Institute on Drug Abuse. Because it undergoes hydrolytic deesterfication into lactic acid, a normal body tissue metabolite, PL has been a favorite synthetic surfical suture material for over 30 years. Kulkarni, R. K., Moore, E. G., Hegyeli, A. F. and Leonare, Fred, Biodegradably Poly(lactic acid) Polymers, J. BioMed. Mater. Res. 5:169–181, (1971); Kulkarni, R. K., Pani, K. C., Neuman, C., and Leonard, F., Polylactic Acid for Surgical Implants, Arch Surg, 93:839–843, 1966. Kulkarni et al found that $^{14}$C-labelled PL to be nontoxic, relatively non-tissue reactive, slowly degraded, entirely metabolized and possibly excreted by the respiratory system. The kinetics of the tissue reactions to PL were comparable stainless steel and Dacron. The degradation of PL is generally attended by a negligible giant cell reaction. Depending upon the mass and surface area of the implant, PL gradually dissolves over a period of 42 to 70 days. Cutright, D. E., Hunsuck, E. E, "The Repair of Fractures of the Orital Floor", Oral Surg., 33:28–34, 1972; Cutright, Duane E., Hunsuck, Ervin E., Beasley, Joe D, Fracture reduction using a biodegradable material, polylactic acid, J. Oral Surgery, 29:393–397, June, 1971. Cutright et al recommended PL sutures even for internal fixations of fractures and emphasized the advantages over stainless steel and other materials that often necessitate removal by a second operation. Implants of biodegradable polylactide (PLA) and polyglycolide (PGA) in experimental bone defects in rats healed in less time than control implanted defects (Hollinger, 1983) Hollinger, Jeffrey O., Preliminary report on the osteogenic potential of a biodegradable copolymer of polylactide (PLA) and polyglycolide (PGA), J of Biomedical Materials Research, 17:71-83, 1983.

In the absence of BMP, induced bone formation does not occur in response to implants of any of the presently known biodegradable polymers. In the presence of BMP in the form of BMP-biodegradable PL polymer delivery system, new bone formation is induced de novo in either extraskeletal and intraskeletal sites. Morphologically, the process is precisely the same in response to BMP in an endogenous delivery system such as demineralized bone matrix proteins as described in previous publications. Mizutani, H., and Urist, M. R., The nature of bone morphogenetic protein (BMP) fractions derived from bovine bone matrix gelatin, Clin. Orthop., 171:213-223, 1982.

The BMP-biodegradable PL polymer delivery system can be spun into sutures and fashioned into plates, screws, slabs, films, and fabrics for use in all kinds of orthopedic, plastic, maxillofacial, neurosurgical and dental reconstructive operations.

The components of the BMP delivery composition of this invention may be varied as desired within a fairly broad range. As shown in Table I, the rate of increase in the volume of new bone induced by the BMP-biodegradable PL polymer delivery composition begins to fall off in the higher range of BMP in the delivery composition. Generally, induced new bone may be noted with as little as about 0.05-0.1 mg. BMP 20 mg biodegradable PL polymer. The upper range of BMP may be varied as required, bearing in mind that the efficiency of the formation of induced new bone falls off with increasing proportion of BMP. As a practical matter, the upper range in the ratio of between about 10-15 mg. BMP/20 mg. physiologically acceptable biodegradable PL polymer in the delivery composition is preferred.

TABLE I

| Mg. BMP/20 Mg. PL | Mm³ New Bone (After 21 Days) |
| --- | --- |
| 0 | 0 |
| 0.1 | 0.4 |
| 0.5 | 4.5 |
| 1.0 | 12 |
| 10.0 | 30.0 |

In practice, the delivery composition is prepared in the desired ratio, and is implanted in the course of a surgical procedure. New bone formation is radiologically observed within about 2-5 days after implant, depending on the subject animal. Bone formation continues to be induced over an extended period.

BMP implant tests performed without biodegradable PL polymer indicate that formation of new bone requires a higher threshold quantity of BMP, and the rate of increase of new bone formation falls off very rapidly above about 5 mg. of BMP in the implant. Table II shows the high threshold of BMP required to induce new bone formation, and the rapid fall off in the rate of new bone formation.

TABLE II

| Mg. BMP | Mm³ New Bone (After 21 Days) |
| --- | --- |
| 0.5 | 0 |
| 1 | 1.0 |
| 2 | 3.0 |
| 5 | 20.0 |
| 10 | 22.0 |

The data in Tables I and II were based upon measurements of gross bone induction in implants in muscle pouches of mice of the quantities of BMP shown.

The invention will be further illustrated by the following examples.

EXAMPLE

Materials and Methods

Bovine BMP (bBMP) was prepared from bovine bone matrix by the method described in the forementioned patent and patent application.

A composite of either bBMP or hBMP (human bone morphogenic protein) in poly(lactic acid) (PL) (Polyscience Ltd. Warrington PA, USA) was prepared as follows. 100 mg quantities of PL were dissolved in 10 ml of chloroform in 30 min. at 24° C. Specified quantities of lyphilized BMP were suspended in the chloroform solution of PL by shaking for 10 minutes. A BMP-PL composite was precipitated by adding 5 ml of absolute ethyl alcohol which initiated the process; 245 ml to complete the process. The composite was allowed to stand in the solution overnight at 24 C., and then separated from the alcohol on Whatman filter paper. The wet BMP-PL composite was inserted into a pellet press to express the remaining alcohol, and air dried overnight. Wet composite was also placed in glass molds to produce flakes, rods, films, or plates. The resulting shaped composite was then examined in vivo to determine its ability to stimulate bone growth de novo by implantation into prepared mouse thigh muscle pouches. Bioassays for BMP activity were then made through these in vivo studies. BMP-PL was also tested for enhancement of repair of bone defects in rodents, dogs, and monkeys.

Samples of BMP or bovine serum albumin without the PL delivery system were implanted in similar host bed test sites for controls. PL controls were similarly implanted in the comparable quantities for the delivery system controls BMP without and with the PL delivery system was implanted in proportions listed in Table III. The implants were excised on day 21, fixed in 10% neutral formation, examined by roentgenographic methods, and paraffin, and stained in hematoxylin, eosin, and azure II.

Results

Table III summarizes observations on implants of PL-free and PL-incorporated BMP. Implants of 0.1 to 0.5 mg of BMP without the PL delivery system were absorbed without inducing visible deposits of new bone; 0.7 mg to 1.0 mg produced deposits of new bone hardly visible in roentgenograms. Increasing the quantities of bBMP from 2.0 to 10 mg increased the quantity of bone with the yields reaching a plateau at about 5 mg.

Figure 2:
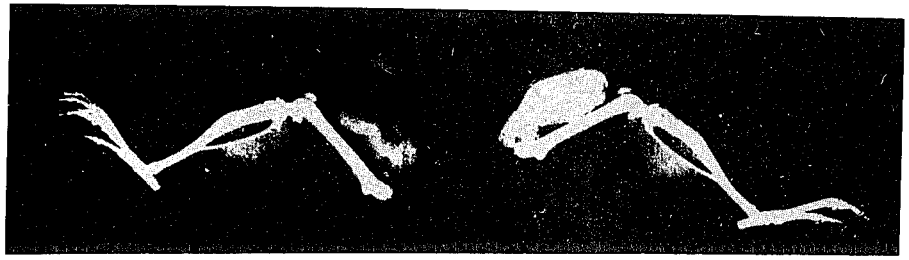
FIG. 2 shows. Roentgenograms of mouse thigh showing implants of 5 mg of bBMP left and 5 mg of BMP/20 mg of bBMP-PLL Note the relatively high radiodensity and field of new bone from the bBMP-PL.
Figure 3:
FIG. 3 shows a photomicrograph of chondroosteoid (C) surrounded by new bone (arrow) and bone marrow, 21 days after implantation of BMP-PL.
Figure 5:
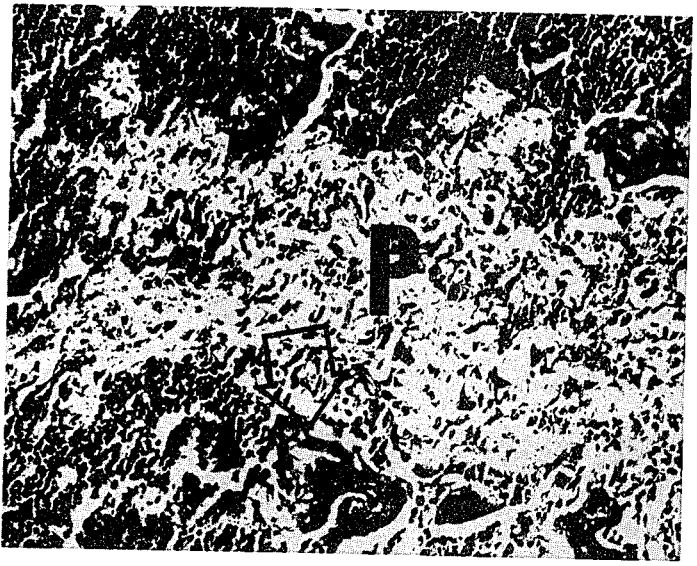
FIG. 5 shows a photomicrograph at high magnification of linabsorbed remnants of BMP-PL. Note: bBMP (arrow) new bone surrounded by bone marrow.
Figure 6:
FIG. 6 shows a photomicrograph of osteoid tissue (O) deposited on surfaces of BMP-PL. Note: bone and bone marrow surrounding remnants of BMP-PL (arrows).

In the PL composite delivery system, as little as 0.1 mg of BMP produced grossly visible deposits; 0.7 mg increased the yields of new bone to 30 times greater than that observed for 0.7 mg BMP without PL. From 1.0 mg the yield was increased 12 times, and from 2.0 mg over 10 times greater than from BMP without the PL delivery system. Doses above 5.0 mg produced somewhat more with than without PL, while 10 mg did not produce more new bone. Thus, below the limits or the capacity of the thigh to either produce or contain new bone, roentgenograms showed that BMP-PL delivery system, produced significantly higher yields of new bone than BMP without the PL. Control implants of comparable quantities of PL without BMP, or albumin without BMP did not induce bone formation (See FIGS. 1 to 2).

Histological sections prepared at 2 to 4 day intervals from 2 to 21 days after the operation showed progressive, dissolution and absorption of the implants. The residual PL consisted of highly refractile of birefringeant fibers. The inflamatory reaction of the tissue to surgical injury subsided within 7 to 14 days. The PL interfibrillary spaces were initially filled with small round cells with densely stained nuclei, macrophages, and fusiform connective tissue cells. Later, an occasionally multinucleated giant cell enveloped the free ends of a PL fibril. By day 21 disintegrating PL fibers on the exterior of the implants were covered with deposits of new bone tissue including hematopoietic bone marrow. In the interior avascular areas of the implants, the fibers were resorbed and enveloped in cartilage or chondrosteoid, which eventually were invaded by sprouting capillaries, resorbed, and replaced by bone in the same sequence of events as occurs in normal skeletal endochondroidal ossification (See FIGS. 3, 4, 5, and 6).

TABLE III

PL-bBMP INDUCED BONE FORMATION IN MOUSE THIGH

| mg/bBMP | New Bone (mm$^3$) | mg BMP/ 20 mg PL | New bone (mm$^3$) |
| --- | --- | --- | --- |
| 0.1 | 0.0 | 0.1 | 0.4 |
| 0.2 | 0.0 | 0.2 | 1.0 |
| 0.5 | 0.0 | 0.5 | 4.5 |
| 0.7 | 0.2 | 0.7 | 6.0 |
| 1.0 | 1.0 | 1.0 | 12.0 |
| 2.0 | 3.0 | 2.0 | 32.0 |
| 5.0 | 20.0 | 5.0 | 30.0 |
| 10.0 | 22.0 | 10.0 | 30.0 |

On the basis of the bone morphogenic responses noted, the BMP-biodegradable PL polymer delivery composition induces formation of new bone by a sequence of morphological events that are observed in implants of BMP without biodergradable PL polymer. Following an initial induction phase for BMP release and for bone formation the half life is about 30 to 90 days but detectable quantities are released until the biodegradable polymer is resorbed. Thus, the induction of bone formation when the BMP-biodegradable PL polymer delivery composition of this invention is used as a bone implant evidences that BMP diffuses out of the polymer and interacts biologically with the host bone tissue to induce a localized bone morphogenetic response.

The delivery compositions of this invention have relatively small masses and are used in relatively thin layers (i.e., in a range of 1 mm to 2 mm in thickness). The heats of solution and polymerization that are encountered in the process of preparing the delivery compositions are insufficent to denature the BMP. The relatively thin layer and small mass allows the heat to rapidly disipate, thereby avoiding an adverse affect on the BMP. Accordingly, the temperature of denaturization of BMP, in the range of 70° C. to 80° C., is not reached under the conditions hereof. However, in preparing larger batches of the delivery composition care must be taken to avoid heats of solution and polymerization that will adversely affect the BMP.

What is claimed is:

1. A composition comprising substantially pure BMP and physiologically acceptable, biodegradable polylactic acid polymer.

2. A composition comprising substantially pure BMP and a physiologically acceptable, biodegradable organic polymer selected from polylactic acid, polylactide, polyglycollic acid, polyglactin or polyglactic acid.

3. A delivery composition for delivering BMP to induce formation of new bone in viable tissue comprising substantially pure BMP and a physiologically acceptable, biodegradable polylactic acid polymer.

4. The delivery composition according to claim 3 to induce formation of new bone in viable tissue wherein the weight ratio of BMP to polymer is at least about 0.05 parts BMP to about 20 parts polymer.

5. The delivery composition according to claim 4 wherein the ratio is at least about 0.1 parts BMP to about 20 parts polymer.

6. The delivery composition of claim 5 wherein said weight ratio is in the range of up to 10 parts BMP to 20 parts polymer.

7. The delivery composition of claim 4 including in said composition a radioopacifying agent.

8. The delivery composition of claim 4 including in said composition an antibiotic.

9. A delivery composition for delivering BMP to induce formation of new bone in viable tissue comprising substantially pure BMP and a physiologically acceptable, biodegradable organic polymer selected from polylactic acid, polylactide, polyglycollic acid, polyglactin or polyglactic acid.

10. The method of preparing a delivery composition for delivering BMP to induce formation of new bone in viable tissue comprising the step of dissolving physiologically acceptable, biodegradable polylactic polymer in a solvent to form a solution, admixing the solution and BMP to form a dispersion, adding a second solvent to the dispersion which causes the precipitation of the polymer and forms a composite of said polymer and said BMP, and removing the solvents from said composite to form said composition, the weight ratio of BMP and polymer being at least 0.05 parts BMP to 20 parts polymer.

11. The method of inducing formation of new bone in viable tissue comprising implanting in said viable tissue a delivery composition comprising BMP and a physiologically acceptable, biodegradable polylactic acid polymer wherein the weight ratio is at least about 0.05 parts BMP to about 20 parts polymer.

12. A method according to claim 11 wherein the weight ratio is at least about 0.1 parts BMP to about 20 parts polymer.

13. A method according to claim 12 wherein the weight ratio is at least about 0.1 parts BMP to about 20 prts polymer.

* * * * *